(12) United States Patent
Eller

(10) Patent No.: US 8,600,903 B2
(45) Date of Patent: Dec. 3, 2013

(54) CONTAINERS FOR TRANSFERRING PRODUCTS AND METHODS FOR THEIR TRANSFER

(75) Inventor: Charles Eller, Lake Saint Louis, MO (US)

(73) Assignee: Express Scripts, Inc., St. Louis, MO (US)

( * ) Notice: Subject to any disclaimer, the term of this patent is extended or adjusted under 35 U.S.C. 154(b) by 128 days.

(21) Appl. No.: 11/818,330

(22) Filed: Jun. 14, 2007

(65) Prior Publication Data

US 2008/0308452 A1 Dec. 18, 2008

(51) Int. Cl.
*G06Q 30/00* (2012.01)

(52) U.S. Cl.
USPC ............. 705/330; 705/28; 705/332; 705/337; 705/336

(58) Field of Classification Search
None
See application file for complete search history.

(56) References Cited

U.S. PATENT DOCUMENTS

| | | | |
|---|---|---|---|
| 4,262,494 A | 4/1981 | Karow, Jr. | |
| 5,417,082 A * | 5/1995 | Foster et al. | 62/457.1 |
| 5,441,170 A * | 8/1995 | Bane, III | 229/103.11 |
| 5,827,385 A | 10/1998 | Meyer et al. | |
| 5,924,302 A | 7/1999 | Derifield | |
| 5,956,968 A | 9/1999 | Grabowski | |
| 5,979,693 A * | 11/1999 | Bane, III | 220/592.2 |
| 6,397,163 B1 * | 5/2002 | Hoyt et al. | 702/136 |
| 6,868,982 B2 | 3/2005 | Gordon | |
| 6,875,486 B2 | 4/2005 | Miller | |
| 6,886,357 B2 | 5/2005 | Gano, III et al. | |
| 6,968,711 B2 | 11/2005 | Smith et al. | |
| 7,028,504 B2 | 4/2006 | Derifield | |
| 7,130,771 B2 * | 10/2006 | Aghassipour | 702/187 |
| 2002/0004724 A1 * | 1/2002 | Eastman | 705/1 |
| 2003/0014994 A1 * | 1/2003 | Smith et al. | 62/371 |
| 2004/0200232 A1 * | 10/2004 | Gano et al. | 62/457.2 |
| 2007/0028642 A1 * | 2/2007 | Glade et al. | 62/371 |
| 2007/0193297 A1 * | 8/2007 | Wilson | 62/371 |

* cited by examiner

*Primary Examiner* — Fateh Obaid
(74) *Attorney, Agent, or Firm* — Bryan Cave LLP

(57) ABSTRACT

Methods, systems, and containers for transporting products, such as medical products are disclosed. The methods and systems involve identifying an environmental condition of a place to where a product is to be shipped, identifying an environmental condition of a place from which the product is to be shipped, identifying the amount of time that the product is expected to be in transit during shipping, and determining the type of container and cooling element that should be employed to transport the product.

24 Claims, 17 Drawing Sheets

* Can change to meet a certain insert thickness requirement

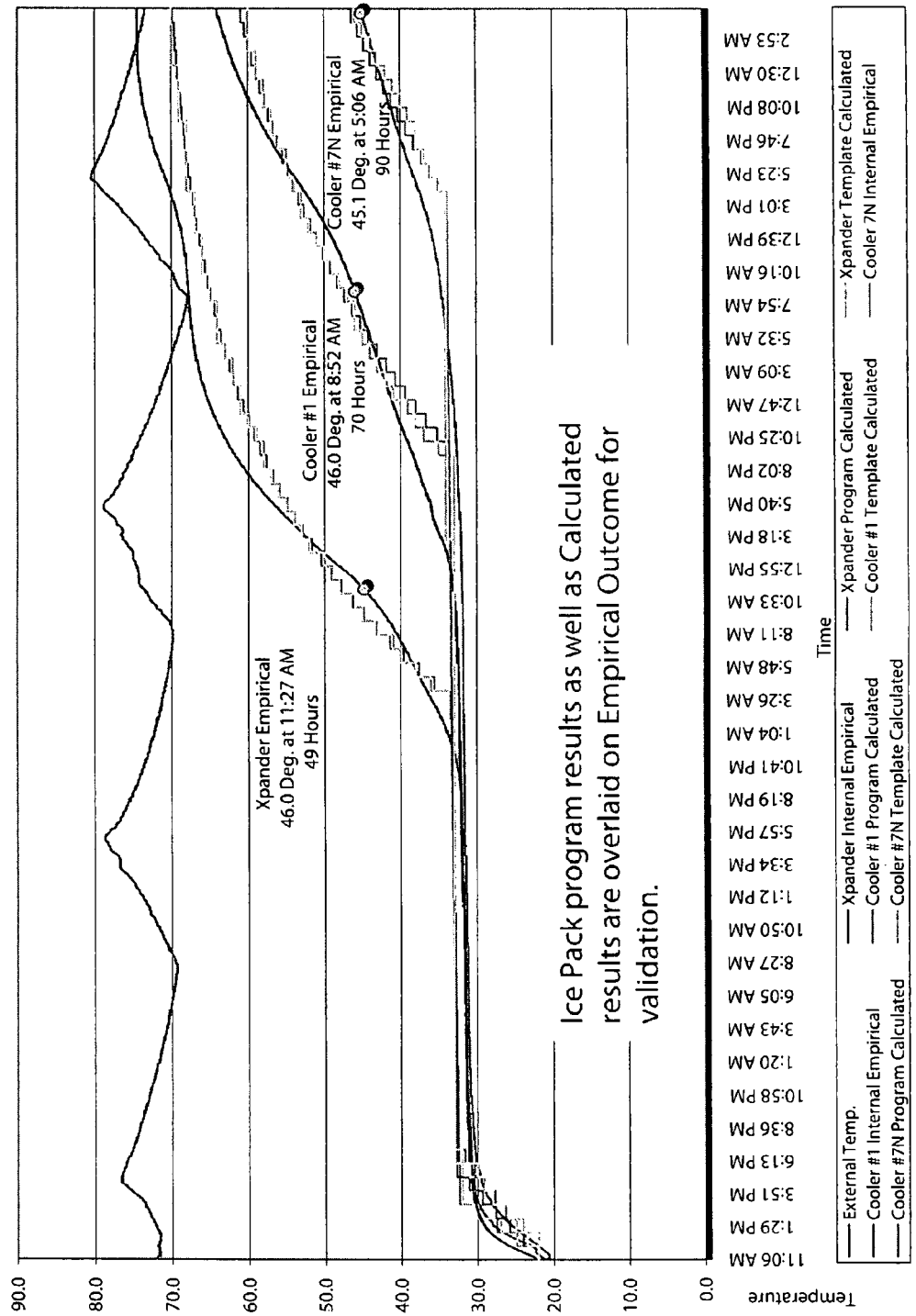

CONTAINERS FOR TRANSFERRING PRODUCTS AND METHODS FOR THEIR TRANSFER

FIELD OF THE INVENTIONS

The present inventions generally relate to methods of transporting and transferring objects and to containers designed for and employed in such methods.

BACKGROUND OF THE INVENTIONS

Transporting or transferring objects from one place to another is generally known to involve considerations of combinations of factors that must be taken into account to ensure the proper and efficient transport of such objects. The factors and considerations, of course, vary depending on the object(s) desired to be transported. For example, physical properties and characteristics, such as weight, size, the physical constitution or make up, and the conditions under which an object should be transported, are some of the parameters that must be considered when one is deciding on the best method for shipping any particular object. Other factors that must be taken into consideration include the parameters of the container to be employed, such as the make up or constitution of the container to be used, the type and amount of cooling or heating, if any, that should be provided for a substance to be transportation, the distance that an object is to be transported, and the weather and environmental conditions that an object or container may be exposed to during its journey, including susceptibility to being altered in different weather conditions and climates.

For many temperature or environmentally sensitive products, such as foods, drugs, body organs, and material samples, it is often desirable to maintain a specific constant temperature, or range of temperatures, during transportation or storage of such objects. In addition, the shipment of multiple temperature sensitive objects in one container, where each object is required to be maintained at a different temperature, is frequently required in the course of transport of objects for medical and scientific research or use. The quantity of material which must be shipped may sometimes be of such small size that delivery by express or courier service is feasible and cost effective, so long as each object can be maintained at its own temperature range. Refrigerating or self-heating containers generally provide relatively constant temperatures or temperature ranges for such products, but tend to be bulky, heavy, and complicated to operate. In shipping, especially by air, the substantial weight of a refrigeration or self-heating container can add excessively to costs.

Various approaches have been taken by the art to address some of the foregoing issues of shipping objects, and have obtained varying results. For example, Karow, U.S. Pat. No. 4,262,494, discloses a system of three containers for the freezing and short-term storage of semen, and other similar tissues, at low cryogenic temperatures after collection and during conventional transportation to a permanent storage facility. According to Karow, tissue straws or tubes, containing the treated tissue, are secured inside a hollow canister of heat conducting material in such a way as to prevent the straws from being in contact with the interior walls of the canister. The canister is then filled with an insulating medium and is secured in an insulated metal box, and the insulated box is surrounded on all sides with a solid freezing medium in a shipping container. The insulating medium in the canister and the insulation of the box are said to be selected for quality and quantity to attain the desired rate of temperature change, but should be of a gas (e.g. air) or liquid which does not change physical form (liquify or freeze) in the temperature range to which it will be subjected and which does not chemically interact with the invention components, including the semen straws. The straws must be secured within the canister in a manner to prevent them from being in contact with any heat conducting materials other than the insulating medium. The insulating medium surrounding the straws, as cooled by the canister walls, is said to provide the controlled-rate of cooling and freezing for the tissue. By varying the quantity and quality of the insulating medium the rate can itself be varied.

Foster et al., U.S. Pat. No. 5,417,082, discloses an insulated container which uses two coolants at different temperatures, such as ice water and dry ice, respectively, disposed on opposite sides of an object. The object is separated from both refrigerants by heat regulators of an insulating material of different thicknesses. It is said that the thicknesses of the insulating material can be varied such that the object is maintained at a specific temperature along a temperature gradient existing between the temperatures of the two coolants. The object may be disposed within a thermally conductive box which maintains a uniform temperature throughout the product. Foster also discloses a shipping container which is said to be able to maintain an object at a constant user-selected temperature within a specified range of temperatures for maintaining a uniform temperature throughout the product. According to Foster, the shipping container may be of a reduced weight which maintains the product at the specified constant temperature for an extended period of time.

Bane III, U.S. Pat. No. 5,441,170, discloses a reusable insulated shipping container which is said to be made of sturdy, lightweight insulated panels, and which is said to be adapted for transporting multiple uniquely temperature sensitive objects in one overall container, over extended time periods, without the need for elaborate temperature control systems. According to Bane, the container is said to isolate each object transported, such that the temperature of each object remains virtually unaffected by the temperature of the other objects being transported. The container may include removable multiple insulated inner containers formed from a plurality of rigid foam panels, and a removable spill containment device, such as a liner, which prevents leakage of liquids and provides additional protective padding. It is also stated that the container allows for shipping a non-temperature sensitive object together with a temperature sensitive object, without affecting the quality of each object.

Meyer et al., U.S. Pat. No. 5,827,385, discloses an evacuated insulation panel or container which may be used for forming an insulated shipping container, and a method of producing the insulated panel or container. According to Meyer, an insulated panel or container also allows for efficiently producing containers with a minimum wall thickness and with a minimum heat transfer. According to Meyer, the evacuated insulation panel or container may be formed in practically any shape and may be rapidly evacuated for obtaining high volume production. In one embodiment, an evacuated insulated container is formed by a pair of opposing and identical insulated panels each of which includes a vacuum formed semi-rigid sheet of gas impermeable plastics material forming a tray or shell having a bottom wall and side walls defining an open top cavity, and the side walls extend to form an outwardly projecting peripheral planar flange. The cavity is filled with an insulation media or material such as silica powder or rigid open cell foam, and a sheet of porous filter material may be placed over the filled cavity and sealed to the flange to hold the powder within the cavity during evacuation. The shell with the insulation is then placed within an evacuation chamber which encloses a platen positioned above the tray, and the platen may be heated. A sheet of gas impermeable plastics material is supported between the platen and the peripheral flange of the shell. After air is evacuated from the insulation media, the cover sheet is pressed and sealed against the peripheral flange by welding or adhesive to form an air-tight sealed cavity enclosing the insulation media. Each shell is provided with inner and outer lip portions on opposite side walls of the shell and with a partial crossover recess, so that two of the insulated panels may be pressed together to form an insulated container defining a chamber for receiving a temperature controlling media such as dry ice and a temperature sensitive article such as a pharmaceutical drug.

Grabowski, U.S. Pat. No. 5,956,968, discloses a cold pack for medicinal vials which includes an outer housing attached to a base, wherein the base has a supporting depression therein for receiving a tray of medicinal vials. The outer housing has a hollow interior for receiving the tray therein. The tray is enclosed by a closure means keeping the tray in a chilled state inside the housing. To further the cooling ability of the cold pack for medicinal vials, the cold pack may be placed within a reclosable insulated bag. The insulated bag can be attached to or placed in the drug case used by medical personnel to transport medicines to the patient's location.

Bane III, U.S. Pat. No. 5,979,693, discloses a reusable insulating panel that can be used in a shipping container to allow temperature sensitive materials to be transported over an extended period of time without the need for external temperature control. The panel is said to separate material being shipped from the exterior shipping container to protect the cargo from objects that may puncture the shipping container, and also provides structural integrity to the shipping container as well as impact protection for the material being shipped. The insulating plate member may be used to separate air compartments, which are co-extensive with the face of the plate member so that convection is not allowed between the compartments.

Miller, U.S. Pat. No. 6,875,486, discloses a packaging system that is said to allow the shipment of objects under low temperature conditions for periods of time of up to 150 hours while effectively maintaining the low temperature conditions and thereby guaranteeing the integrity, wholesomeness and officiousness of the products being shipped. Miller discloses a package construction that utilizes two or more radiant barriers separated in the packaging by a container in combination with suitable insulation. Within the inner radiant barrier is contained two or more phase change materials which are said to change phase at different temperatures. The outer radiant barrier covers the exterior of the packaging. The packaging system is characterized wherein the first phase change material has a phase change at minus 20 degrees centigrade, and wherein the second phase change material has a phase change at zero degrees centigrade. The phase change materials may be in the form of gel packs. The container is a rigid construction made of corrugated cardboard with its exterior completely covered with the first radiant barrier in the form of a film bonded to the cardboard. The insulator is preferably plastic foam. The packaging system has the second radiant barrier in the form of a flexible container, such as a bag or pouch, comprised of an outer laminate of radiant barrier material and an inner laminate of plastic durable at low temperatures.

Gano III et al., U.S. Pat. No. 6,886,357, discloses a container for storing an item that includes an insulating material defining an interior, the insulating material having a bio-based polyurethane; and a temperature-maintaining material disposed within the interior, the temperature-maintaining material being arranged to maintain a temperature of an item placed with the interior.

Smith et al., U.S. Pat. No. 6,968,711, discloses sorption cooling devices and temperature-controlled containers incorporating sorption cooling devices, particularly temperature-controlled shipping containers for the transportation of temperature sensitive products. The sorption cooling device is said to include a liquid supply apparatus that is responsive to changes in the ambient temperature. The apparatus includes a rigid housing, a first flexible pouch disposed within the rigid housing that contains a high vapor pressure substance, a second flexible pouch enclosing a supply liquid and disposed within the rigid housing adjacent to the first flexible pouch and a liquid conduit for providing liquid communication between the second pouch and an evaporator. The high vapor pressure substance causes the first flexible pouch to exert pressure on the second flexible pouch and assist in the flow of liquid from second flexible pouch to the liquid conduit. Increases in temperature increase the vapor pressure within the first flexible pouch, thereby increasing the flow rate of the liquid and the cooling rate.

Derfield, U.S. Pat. No. 7,028,504, discloses containers for shipping temperature sensitive products in a refrigerated and/or frozen condition for an extended period of time. The containers may be constructed of, for example, rigid polyurethane foam for, among other purposes, small and large shipments, such as via air freight, including via LD3 shipping containers. The containers are formed of a bottom, preferably with a tray for holding product, four sides, and a lid, and preferably with a coolant tray. The bottom, sides and lid are designed to interlock (the sides and base preferably are slide locked or are tongue and grooved, as versus typical 45 degree corners that do not lock together or "grip" together), so as to reduce thermal convection. The coolant tray is a slide-in tray which contains a suitable coolant such as dry ice or gel packs, and which also is made of rigid polyurethane foam and to maintain the coolant out of direct contact with the product. The interior walls and bottom of the container can be configured to provide a convection design to create a controlled air flow within the product compartment, and this air flow can reduce the temperature gradient within the product compartment and thus provide better and even temperature control when shipping biological and other products. Each of the foregoing documents is incorporated herein by reference in its entirety and for all purposes as if set forth fully again.

As will be appreciated from the foregoing, various attempts have been made to address many of the issues encountered in designing containers and methods for transporting objects and have produced varying results. But a problem remains in cases where a product to be shipped must be maintained at a constant temperature range, such as about room temperature. When coolants are placed into containers and various forms of packages, quite often the coolant decreases the temperature of the product to be shipped below the desired temperature range. If, on the other hand, the coolant is not included in the package in the proper amount, the product to be transported may acquire a temperature above the desired temperature range during transport. In either event, shipping products at temperatures outside of optimal ranges will often result in deleterious effects being imparted to the products and, in particular, possible hazards to customers who are requesting and relying upon health care products.

Thus, there is still a need for a method for transporting products that addresses concerns and issues noted above and provides for the expeditious and economically efficient transfer of objects, such as, in particular, medicaments and objects that may be subject to spoiling.

SUMMARY OF THE INVENTIONS

Accordingly, the present inventions provide methods and containers for shipping objects, such as health care products, which may generally be sensitive to climate conditions and environmental effects, so that the objects can maintain proper efficacy. More particularly, the present inventions provide methods and containers for transporting objects, which are generally sensitive to environmental conditions, at controlled temperatures.

In one embodiment, the present invention provides methods for determining an appropriate container and cooling element to be employed in transporting goods from one location to another. Thus, the present invention provides a method which includes identifying environmental conditions of a place where a product is to be shipped (e.g., a place of destination), identifying environmental conditions of a place from which a product is to be shipped (e.g., a place of origination), identifying the amount of time that the product is expected to be in transit between the place of origination and the place of destination, and determining the type of container and type and amount of cooling or heating element that should be employed to transport one or more products.

In another embodiment, the present invention provides a means for receiving information from a requesting source, and for using the information received to identify the environmental conditions (such as the temperature) of a place to which a product is to be shipped, and for identifying the environmental conditions (such as the temperature) of the place from which a product is to be shipped, and for identifying the amount of time that a product that has been requested will be in transit, and for determining the type of container and cooling element that should be used to transport one or more products. The present invention may further include a combination that includes means for receiving information from a requesting source, means for using the information received from the requesting source to identify the environmental conditions of a place to which a product is to be shipped, means for identifying the environmental conditions of the place from which a product is to be shipped, and means for using the information to determine the type of container and type and amount of cooling element that should be used to transport one or more products.

The present invention further provides a method and a container for transporting products, such as medicaments, that should be kept within a temperature range of from about 59° F. to about 86° F., or within a temperature range of from about 36° F. to about 46° F. The container may include heating or cooling elements. The heating or cooling elements may be separated from the product(s) to be transported by a barrier element. The combinations and arrangements allow the product(s) to remain at a relatively constant temperature range such as during a period of transportation.

In another embodiment, the present invention provides a method for preparing a container for transporting a product which includes identifying environmental conditions of a place where a product is to be shipped, identifying environmental conditions of a place from which a product is to be shipped, identifying the amount of time that the product is expected to be in transit, determining the type of container and cooling element that should be employed to transport a particular product, and constructing a container in accordance with the information.

In a further method according to the present invention a heating or cooling element is placed into a container after which an insulating element is placed in the container to substantially enclose the heating or cooling element in the container, and then the product is placed into the container positioned at a position so that it is substantially separated from the heating or cooling element. The product may then be shipped in accordance with the present invention. The present invention thus includes containers prepared in accordance with the methods discussed above.

BRIEF DESCRIPTION OF THE DRAWING FIGURES

Figure 7A:
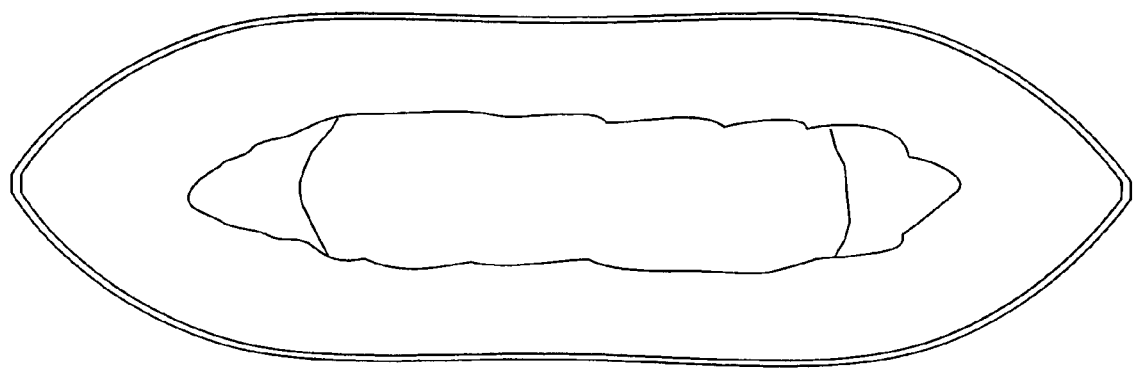

FIGS. 7(a), (b), and (c) are side view illustrations of an Xpander Pack being prepared in accordance with the invention.

Figure 8:
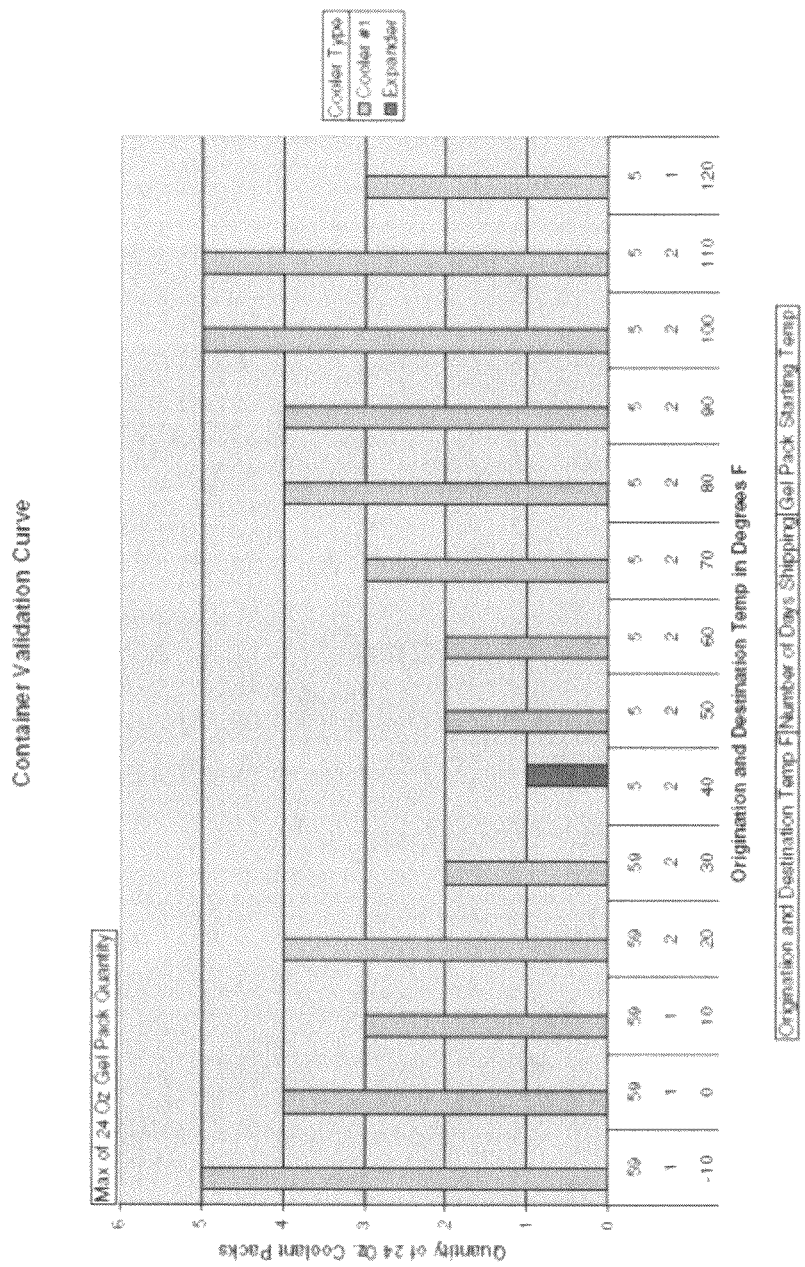

FIG. 8 is a graph showing a comparison of a #1 cooler and an Xpander Pack with regard to origination and destination temperatures versus the quantity of cooling elements employed.

Figure 9:
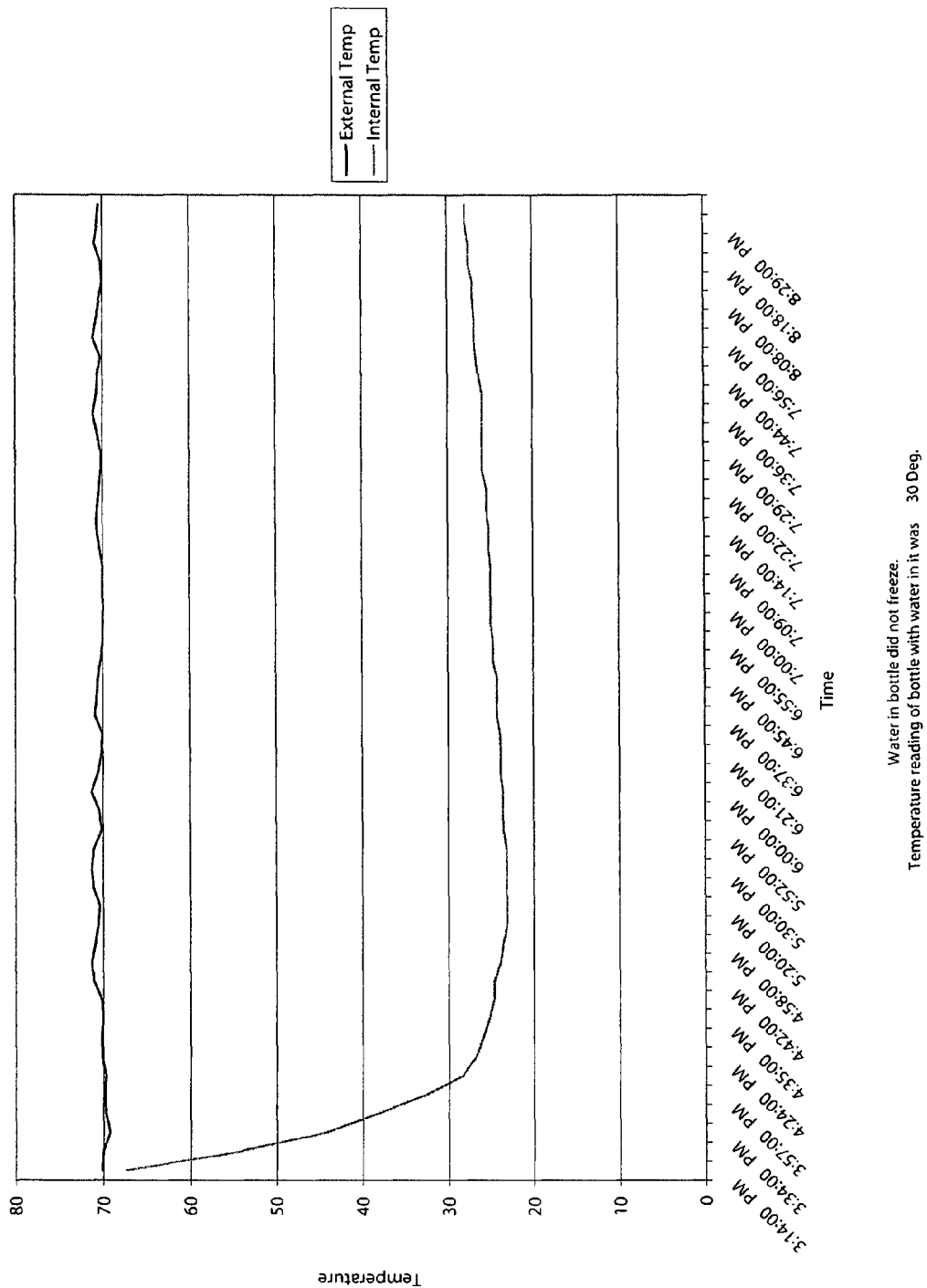

FIG. 9 is a graph of a freeze test in a #1 cooler having 5 cooling elements.

Figure 10:
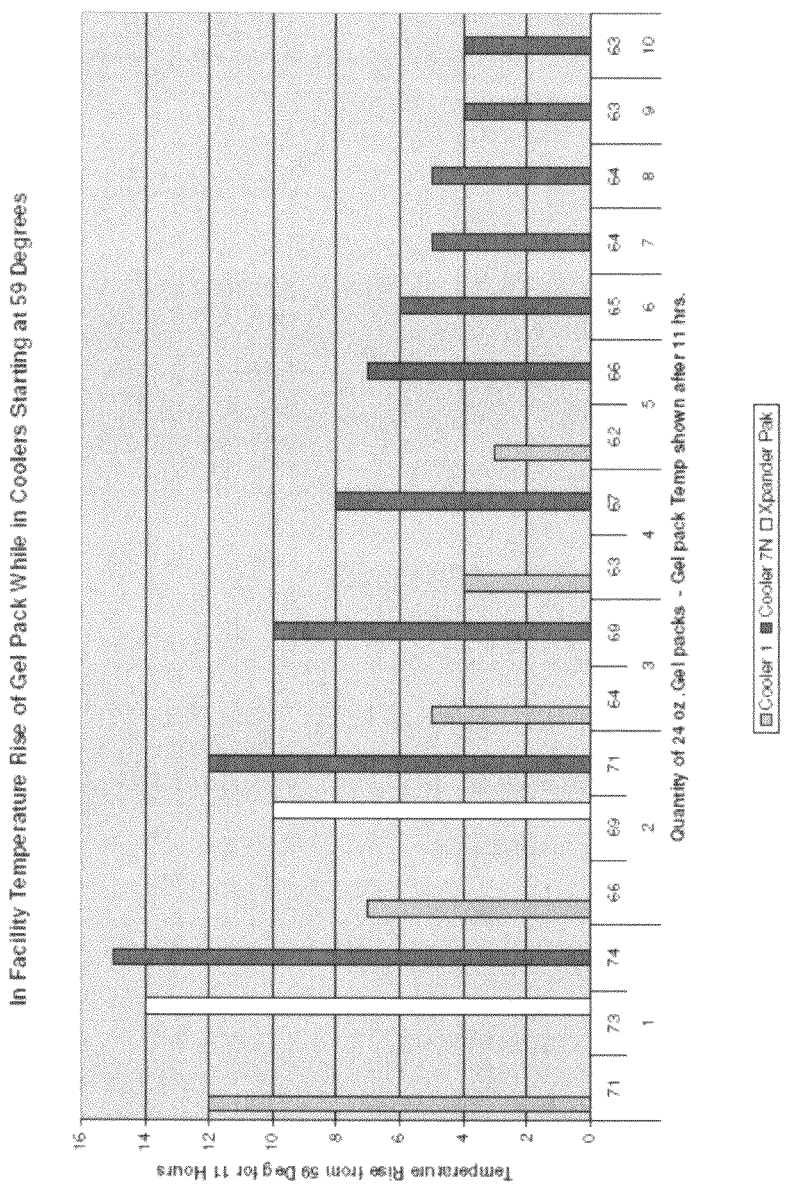

FIG. 10 is a graph illustrating the rise in temperature of Gel Packs in the #1 coolers, #7N coolers, and in Xpander Packs.

FIG. 11 is a graph illustrating a comparison of actual and projected empirical temperature ranges in containers according to the invention.

DETAILED DESCRIPTIONS OF THE INVENTIONS AND DRAWING FIGURES

In general, when a package according to the present invention is being transported, warm external/exterior conditions, or cold external/exterior conditions, will transfer heat to, or withdraw heat from, respectively, the product side of a package containing a product. If, for example, the external conditions are warm or hot, such that the external temperature is higher than the internal temperature of a package, for example when the package has a cooling element, the heat obtained by the product side of the package will be transferred to the cooling element inside the package. If, for example, the external conditions are warm or hot, and the package has a cooling element, and a barrier or insulating element that separates the product from the cooling element, the product side of the package, in turn, will transfer the heat it acquires from the external environment through the barrier or insulating element to the cooling element side of the package, so that the product side decreases in temperature and the cooling element side absorbs the heat transferred.

When there is a barrier element, the transfer of heat from the product side of the container to the cooling element side of the container occurs at a controlled rate through the internal barrier or insulating element. When the cooling element is a frozen cooling element, such as an ice pack or a frozen gel pack, it has a greater capacity to absorb heat from the product side of the package without increasing substantially in temperature. That is because, generally speaking, it takes about 80 times the amount of heat to raise the temperature of a frozen cooling element, such as an ice pack or a frozen gel pack, by 1° F., as it takes to raise the temperature of a liquid or fluid cooling element, such as a liquid gel, by 1° F.

The present inventions provide methods and containers for shipping objects, such as health products, for example, medicaments, pharmaceutical products, and nutriceutics, which may generally be sensitive to environmental conditions, such as, climate conditions, including temperature changes, so that the objects being transported can maintain proper freshness and efficacy during transportation. As used herein, the term "container" is meant to include any type of vehicle for transporting an object including coolers and envelope-type packages.

In one embodiment, the present invention provides methods for determining an appropriate container, and type and amount of cooling element or heating element, to be employed in transporting goods from one location to another. Thus, one method includes the steps of identifying environmental conditions of a place where a product is to be shipped, identifying environmental conditions of a place from which a product is to be shipped, identifying the amount of time that the product is expected to be in transit, and determining the type of container, and/or the type and amount of cooling element(s) or heating element(s), that should be employed to transport one or more products.

Another embodiment provides a means for receiving information from a requesting source and for using the information received to identify the environmental conditions of a place to which a product is to be shipped, and for identifying the environmental conditions of the place from which a product is to be shipped, and for identifying the amount of time that a product that has been requested will be in transit, and for determining the type of container and cooling element that should be used to transport one or more products. Alternatively, a combination of one or more means may be employed, such as means for receiving information from a requesting source, means for using the information received from the requesting source to identify the environmental conditions of a place to which a product is to be shipped, means for identifying the environmental conditions of the place from which a product is to be shipped, and means for using the information to determine the type of container and cooling element that should be used to transport one or more products.

Generally, the means for receiving information may be any means capable of receiving information known in the art. For example, an individual, such as a potential customer, may simply access a particular website that allows an individual to place an order or request goods or services. The website, then, will have standard areas or fields that require information, such as, name, address, billing information, type or product or service requested, prescription information, amount(s) of products to be requested, and place that a product is to be shipped or a service is to take place. The request may then be sent to a receiving means, such as a receiving computer having a program designed to receive and identify particulars of the information sent, or may alternatively simply be an individual who inputs the information received, which begins the process of filling the request for a product or service. The information received about the product or service and the place to which the product is to be forwarded, including the time for delivery, such as one, two, three, four, or five days, may be used and factored together with the forecasted environmental conditions that the product is likely to encounter during its route of transportation. Thus, for example, the forecast, such as the temperature, of the place of origin of the product is identified, the route and method of transport is identified, the temperature(s) or temperature range likely to be encountered during the period of transport is identified, and the forecast, such as the temperature, of the place that the product is to be shipped, also is identified.

The means for receiving and using the information sent, identifying projected temperatures that the container will be exposed to during its delivery, and suggesting the type of container and/or design of container, and/or amount of cooling or heating element that should be employed, if any is required, may be the same or may be different means, such as the same general computer program designed to accomplish all of the foregoing or may be different computer programs designed to acquire and analyze such information. Thus, such a program may identify, through access to weather forecasting and/or reporting databases, such as those publicly available through the internet, the temperature(s) of the place that a product is to be delivered, and/or the temperature of the place from which a product is to be sent from for delivery, and/or the temperature(s) likely to be encountered during the route of transport. The program may then, based on the amount and type of product requested, suggest a particular container, or type of container, or the design that a particular container should have, for efficiently and effectively transporting the product(s) requested. Thus, the program may include data based on the known abilities or capacities of certain materials to transmit heat or prevent the transmission of heat. The program may also include data based on the known abilities of known cooling elements and heating elements to receive heat, and transfer heat, respectively. Thus, the program may also suggest, based on the information received and acquired, the type and amount of cooling or heating element that should be employed to transport a product.

Alternatively, a consumer may request a product by telephone and, in response to a series of questions and prompts by a person or an automated program, such as regarding typical prescription information, including product identification and number, and place of delivery, and numbers of days or period for delivery, the information is input into a program. The program then performs the appropriate calculations or analysis and determines the most cost efficient method of transportation. Alternatively, a consumer may simply download and fill out a standard form and submit the request which will be input into a program as mentioned above.

The foregoing information may be employed to determine, and/or construct, an appropriate container to transport a particular product(s) requested. This may be accomplished by the same program, or by a different program, or by a combination of programs, which would further include information, where necessary, regarding whether a cooling or heating element should be included in the container with the product(s) to be transported and what amount of such element should be included. Thus, a selection of appropriate preconstructed containers may be employed to transport a product, or a container may be custom constructed to satisfy the requirements of the product(s) to be delivered. As will be appreciated, the shipping container can be in the form of a traditional box, a cylindrical tube, a shipping envelope, or virtually any other form that is useful for transporting goods.

One method, then, for preparing or selecting a container for transporting a product, and optionally whether a cooling or heating element should accompany such product, includes the steps of identifying environmental conditions of a place where a product is to be shipped, identifying environmental conditions of a place from which a product is to be shipped, identifying the amount of time that the product is expected to be in transit, and optionally the environmental conditions the product is likely to encounter during transport based on the route of transport, determining the type of container and cooling or heating element that should be employed to transport a particular product, and selecting or constructing a container accordingly.

While programs could easily be designed, in view of the foregoing teachings, to access and combine all the relevant information and determine an appropriate container and cooling or heating element to be employed, in view of the types of containers typically used today to transport goods, and in particular healthcare products, such as pharmaceutical products, one method, which should be viewed in light of the accompanying drawing figures, for combining such information received and acquired and for determining the construction that a particular container should have for transporting a particular product, involves the formula $(a)(k)(\Delta t)/(th)$, wherein a=the sum of the area of the exterior wall surfaces of a container for containing a product;

k=the measure of heat absorption capacity of the material that makes up the container walls;

th=the thickness of the container walls;

$\Delta t$=the difference in the temperature between the external temperature (outside of the containers) and the internal temperature (inside of the container).

The formula $(a)(k)(\Delta t_1)/(th)$ represents the energy lost or gained by a cooling element (e.g., an ice pack or gel pack) or heating element over a given period of time (e.g., BTU lost or gained/time (e.g., in 1 hour)).

Figure 1:
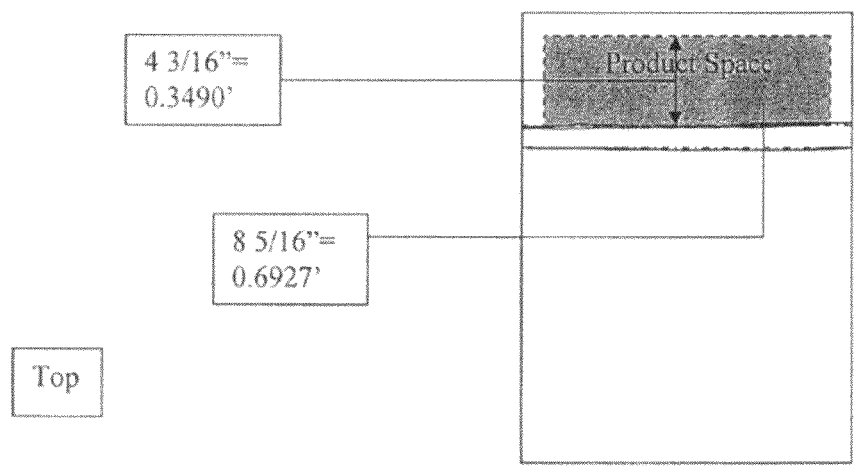
FIG. 1 is a top view of an Xpander Pack envelope-type container showing the length and width dimensions for the product space and showing a barrier element.
Figure 2:
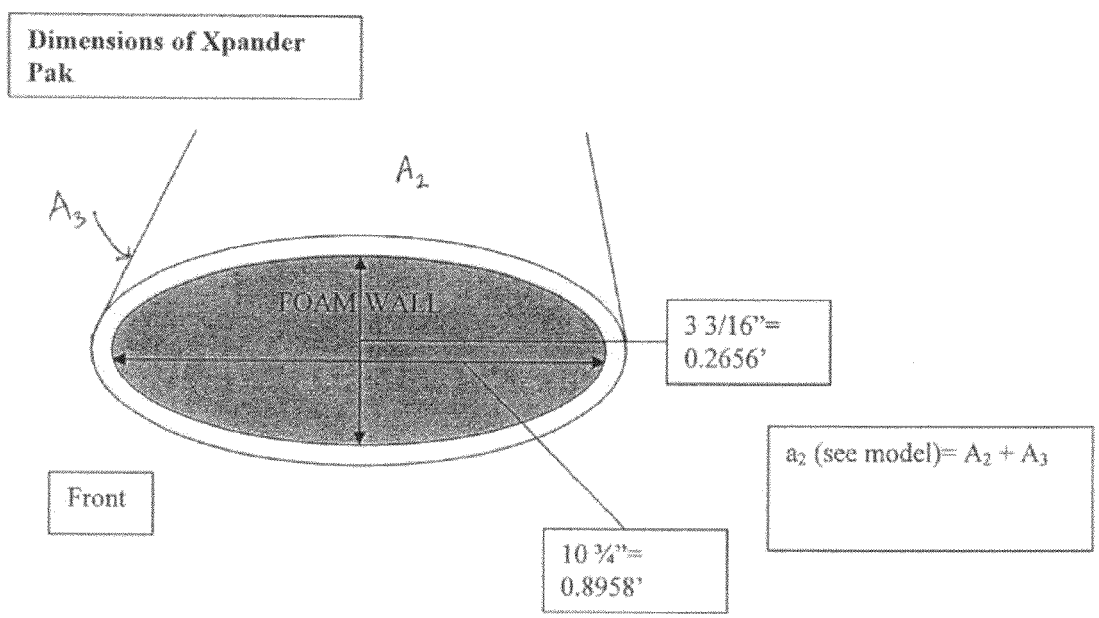
FIG. 2 is a cross section view of an Xpander Pack envelope-type container showing the approximate width and height of the envelope having a foam barrier element.
Figure 3:
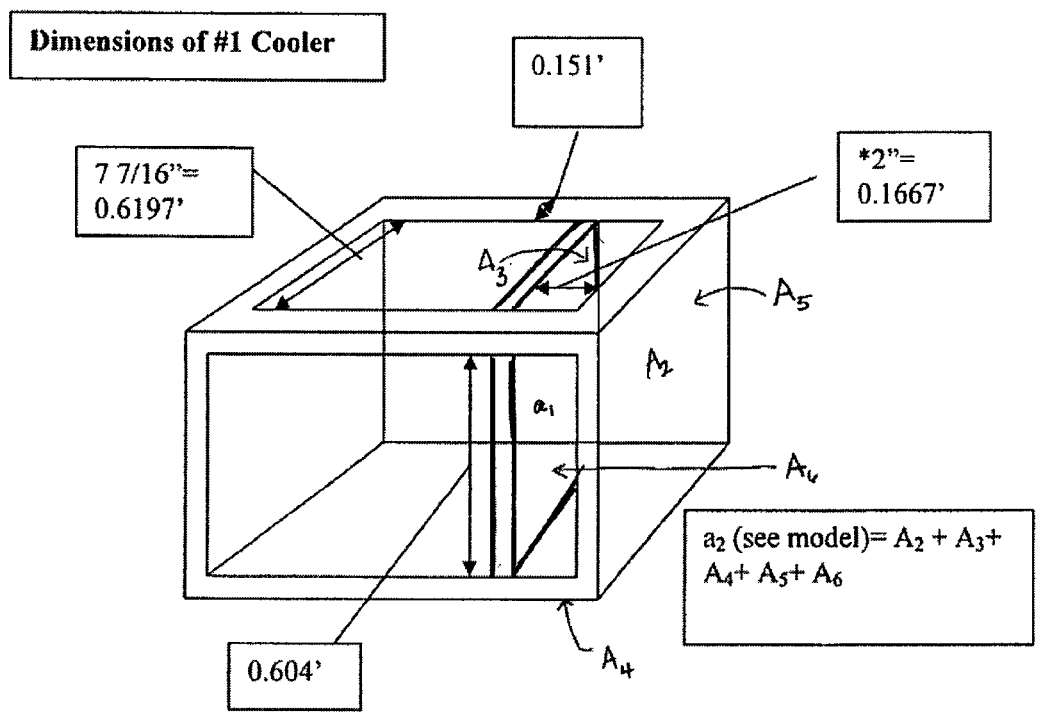
FIG. 3 is a diagrammatic three dimensional view of a #1 cooler type container showing various wall sections of the container.
Figure 4:
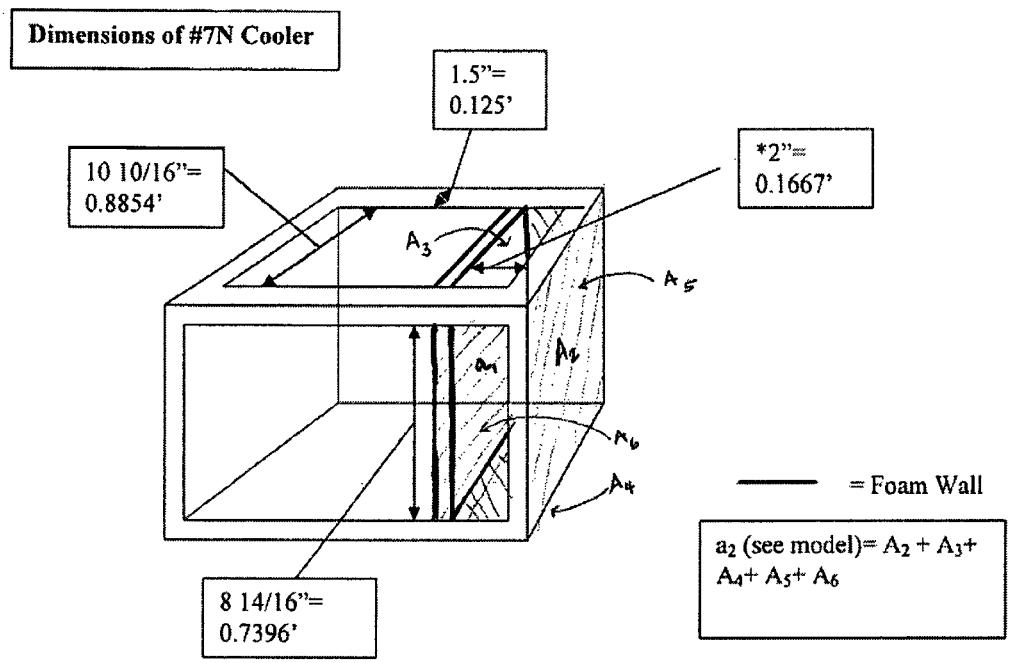
FIG. 4 is a diagrammatic three dimensional view of a #7N cooler type container showing various wall sections of the container.
Figure 5A:
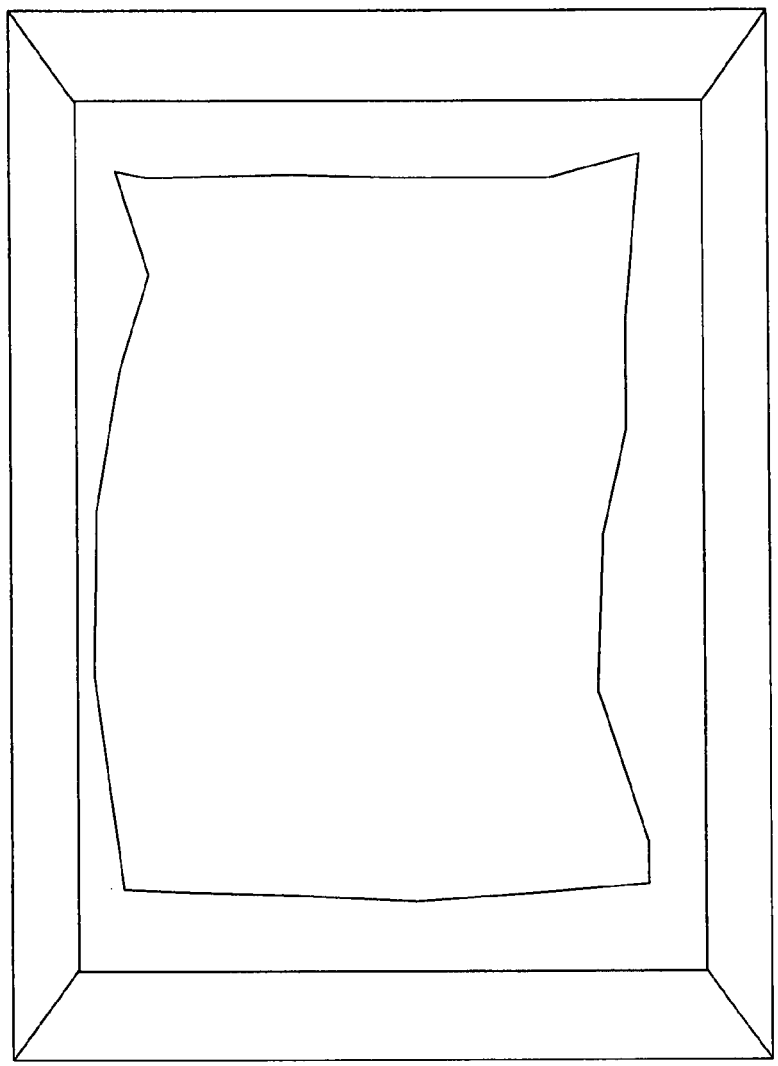
FIG. 5(a) is a top view of a #1 cooler having one cooling element.
Figure 5B:
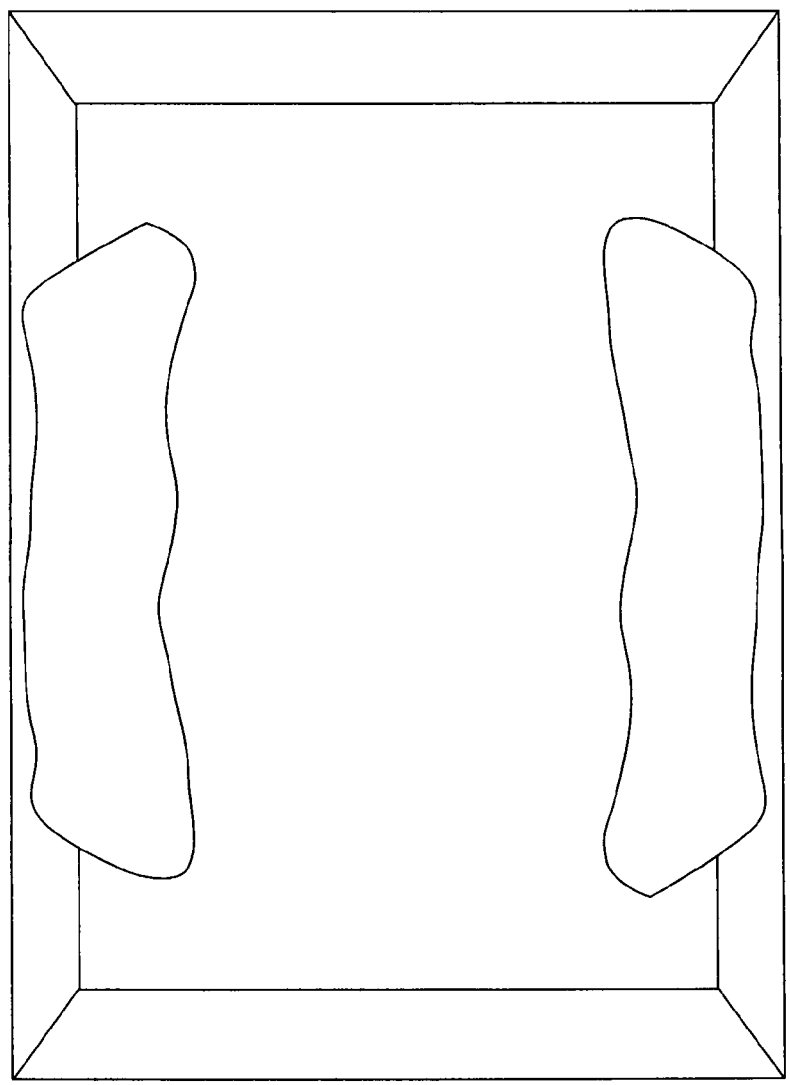
FIG. 5(b) is a top view of a #1 cooler having two cooling elements.
Figure 5C:
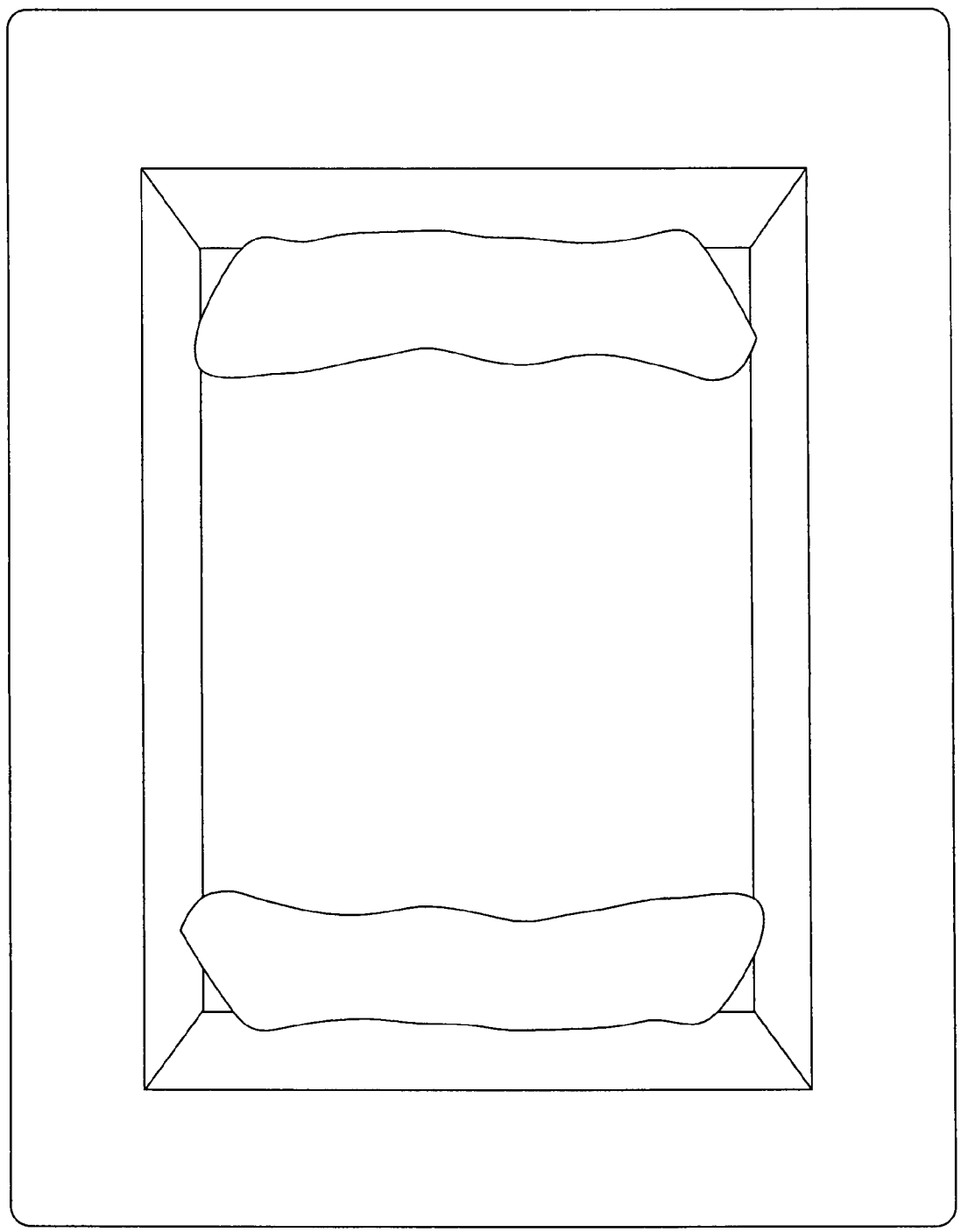
FIG. 5(c) is another top view of a #1 cooler having two cooling elements.
Figure 5D:
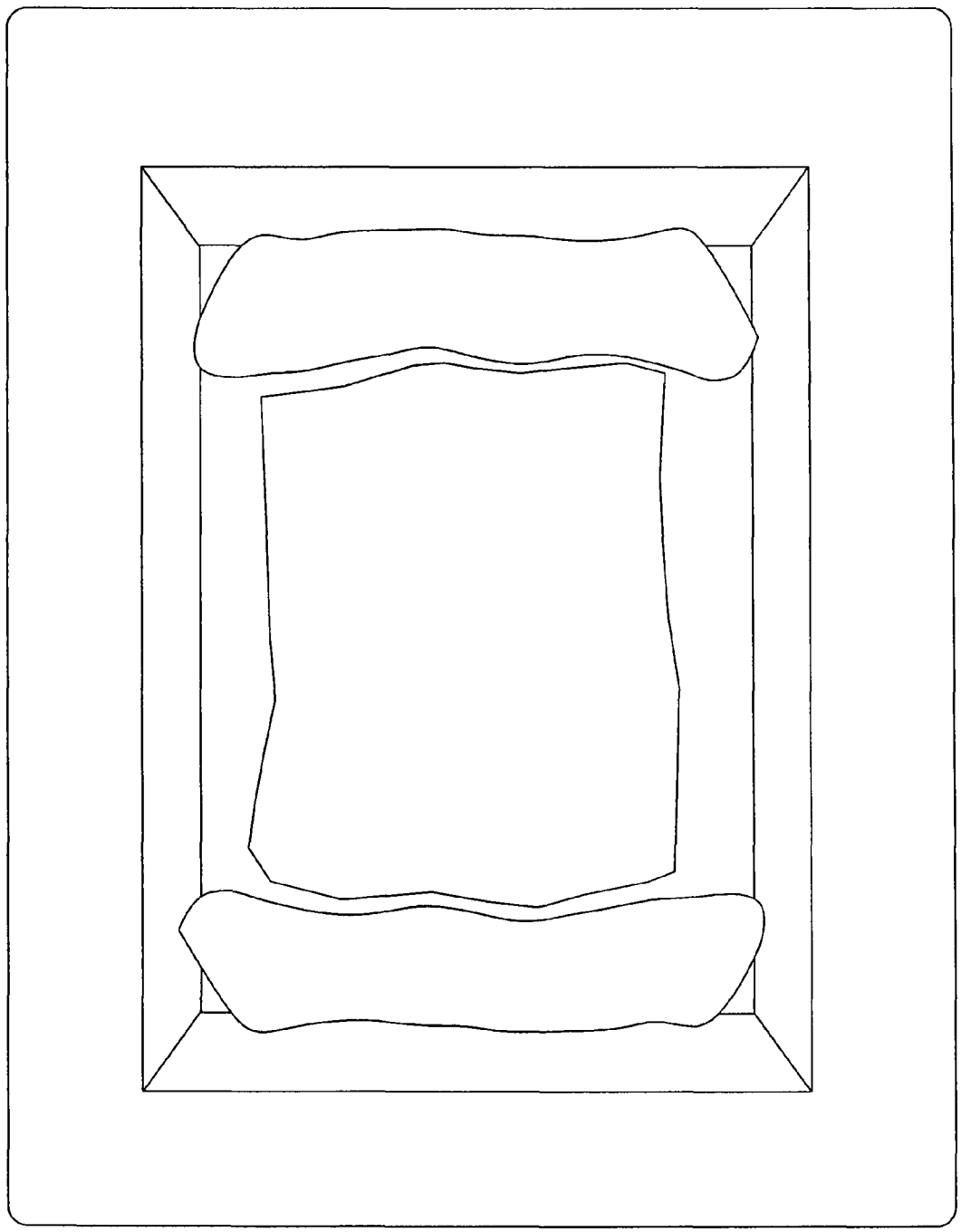
FIG. 5(d) is a top view of a #1 cooler having three cooling elements.
Figure 5E:
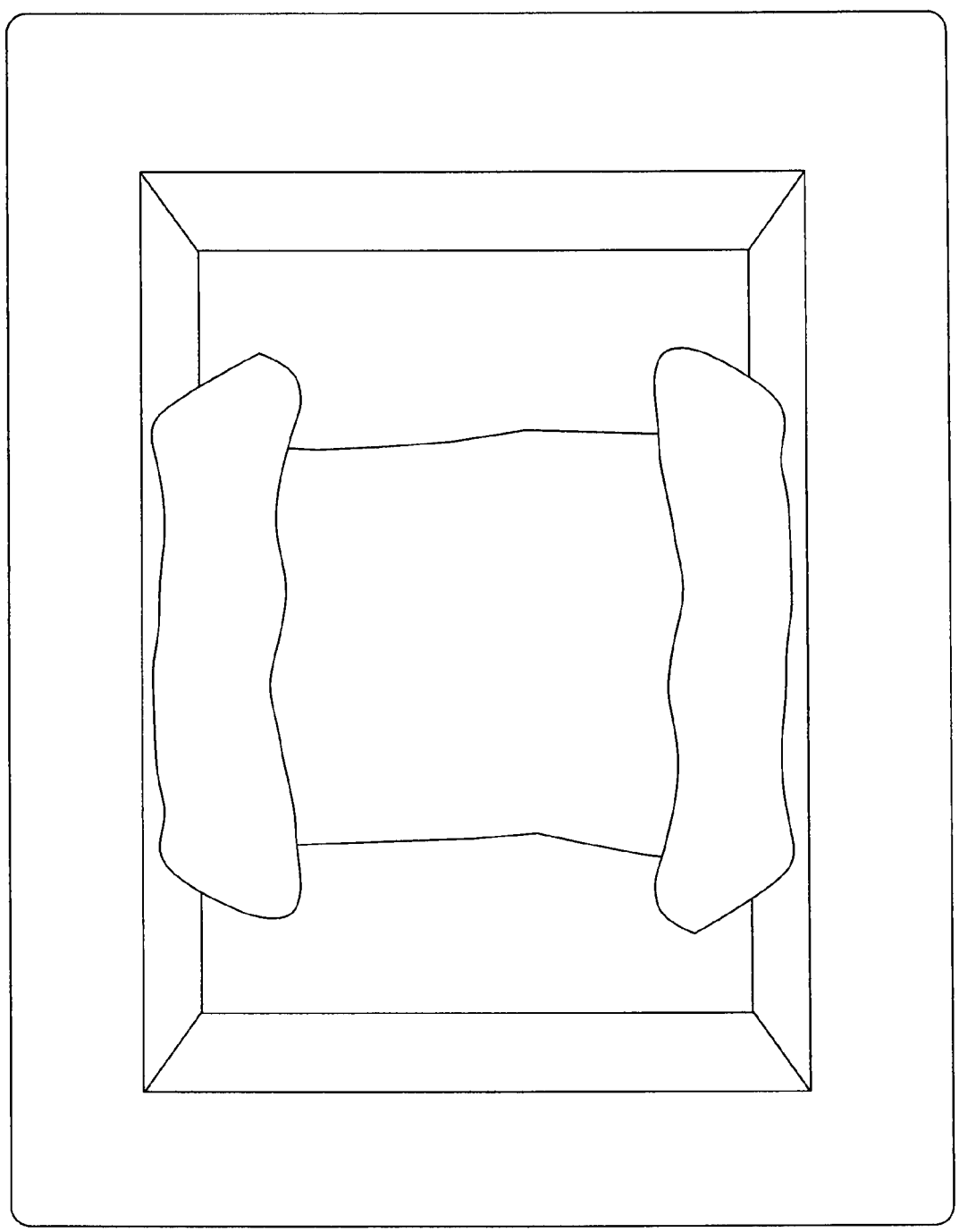
FIG. 5(e) is another top view of a #1 cooler having three cooling elements.
Figure 5F:
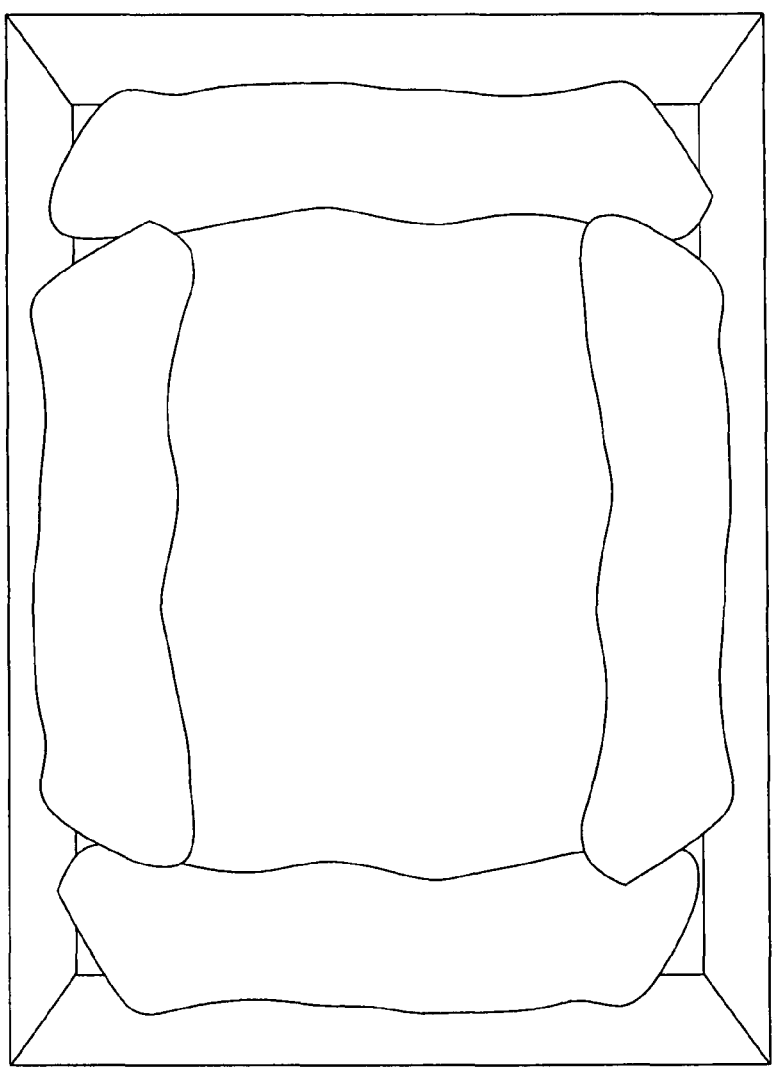
FIG. 5(f) is a top view of a #1 cooler having four cooling elements.
Figure 5G:
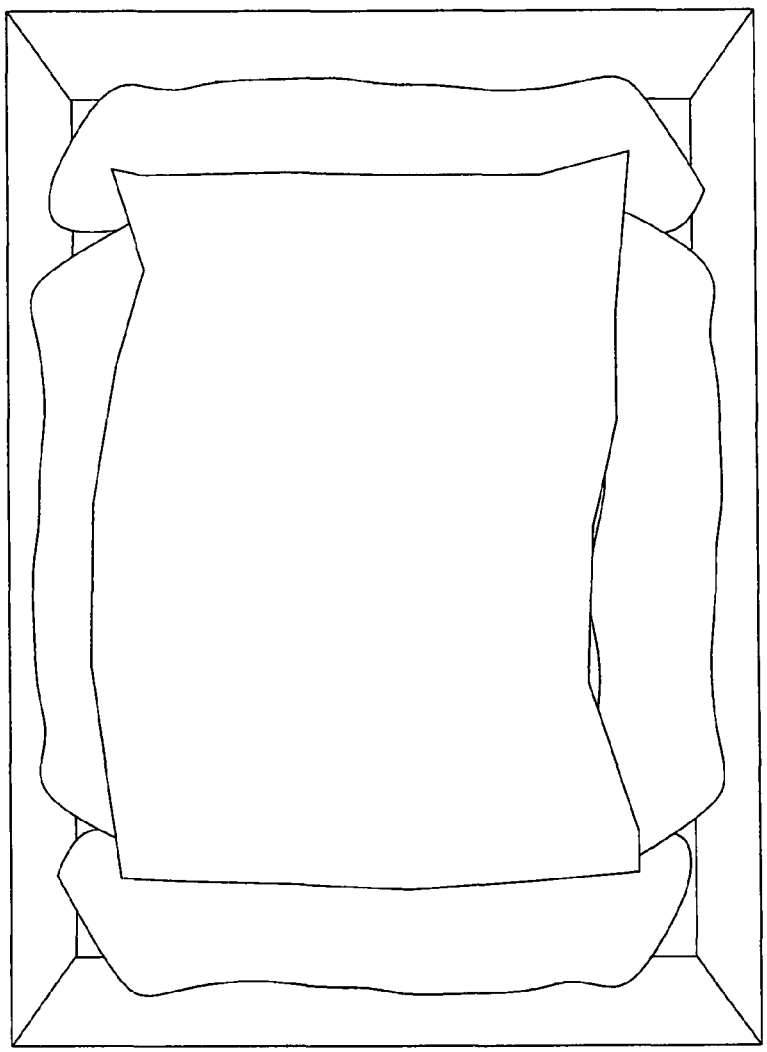
FIG. 5(g) is a top view of a #1 cooler having five cooling elements.

In an embodiment where a container includes a dividing or barrier wall between the product and a heating or cooling element inside a container, the equation employed is $(a_1)(k_1)(\Delta t_1)/(th_1)=(a_2)(k_2)(\Delta t_2)/(th_2)$ wherein:

$a_1$=area of dividing wall;

$a_2$=sum of exterior surfaces of cooler that form the product compartment (see diagram of FIGS. 1-3);

$K_1$=measure of heat absorption capacity of materials of a wall insert;

$K_2$=measure of heat absorption capacity of material of cooler wall;

$th_1$=thickness of wall insert;

$th_2$=thickness of cooler wall;

$\Delta t_1$=Ext Temp$_1$-Int Temp$_1$;

$\Delta t_2$=Ext Temp$_2$-Int Temp$_2$;

Int Temp$_1$=temp of medication compartment;

Ext Temp$_1$=temp of ice compartment;

Int Temp$_2$=exterior temp; and

Ext Temp$_2$=temp of medication compartment

In this regard, the present invention also provides a method and a container assembly for transporting products that should be kept within a controlled temperature range, such as, for example, at a temperature range of from about 59° F. to about 86° F., or within a temperature range of from about 36° F. to about 46° F. The container may include a heating or cooling element which may be separated from the product(s) to be transported by a barrier or insulating element, such as a foam barrier or insulating element. The combination allows the product(s) to remain at a relatively constant temperature range, such as, for example, at or near ambient or room temperature. While the order of operations in constructing a container is not critical, a container may be constructed, for example, by placing a cooling element, such as a Gel Pack or an ice pack, such as a Polar Pack™, or a Cool Pack, into a container after which an insulating element may be placed in the container to substantially enclose, or partition off, the cooling element in the container from a container product area, and then the product is placed into the container positioned at a position so that it may be substantially separated from the cooling element in the container. The container is then sealed or enclosed.

The shipping system according to the present invention thus takes into account the dimensions of the package to be transported, the composition of the package employed to transport the product, the area inside the package, the distance and time that will be required to transport the object from its place of origination to its final destination, and the amount of cooling element in the package sufficient to keep the product in the desired temperature range, or to keep the cooling element side of the package at a temperature of about 32° F., for the duration of the shipping process. The cooling element will continue to absorb the heat in the package that would have otherwise heated and increased the temperature of the product during the shipping period. Thus, the product to be transferred may maintain a temperature in a range of from about 59° F. to about 86° F., preferably from about 68° F. to about 77° F. When a cool temperature range is required, the product may, for example, be transported at a temperature in a range of from about 36° F. to about 46° F.

To assist in achieving the goals of generally accurate and controlled temperature range transport of products, a software program, such as a Java script, Pearl, or C++, may conveniently be employed in accordance with the teachings herein. One such program was designed to calculate and determine the amount of cooling element needed to maintain a particular product in a particular package at a particular temperature range during a particular transport (defined by time of transport and path and environmental conditions of the area of transport). The software is generally of three different program types: (1) the Ice Call Application, (2) the Ice Packaging Application, and (3) the Ice manifest Application. Generally speaking, the Ice Call Application allows a caller to set up and request delivery date of packages that require, for example, the cooling element be ice. The Ice Packaging Application allows an individual, such as a packer, who will provide, or assist in providing, for filling the order, to scan and account for the requested product, generate any labels required, and the specifics of the container type and cooling element, such as ice. The container type and the type and amount of cooling element are determined by the duration of travel expected in combination with a comparison of the temperatures of the point of shipping origination and the point of shipping destination. The Ice Manifest Application is employed by a source, such as an individual, to weigh the completed package and to generate any labels required for the package. Typically, products will be shipped in one to five days, preferably one or two days.

More particularly, a series of experiments were conducted in which different package materials (packages) were filled with various types and amounts of cooling elements, and the sealed packages were subjected to various temperature ranges over a period of time on the order of one to five days. Changes in temperature, both externally and internally, were generally measured for each of the different packages containing different cooling elements therein and were generally measured on the hour, or about half hour. The amount of energy lost or gained over time by the cooling element was identified according to the formula $(a)(K)(\Delta t)/(th)$. Thus, starting with one particular type of package, such as, for example, a #7N cooler, or a #1 cooler, or an Xpander Pak, and one type of cooling element, such as a typical 24 ounce ice pack or gel pack, the change in internal temperature of the container was measured over time.

Generally, from one to six (i.e., 1, 2, 3, 4, 5, 6) 24 ounce ice packs or gel packs were variously employed as cooling elements in the foregoing experiments. The period of time over which temperatures were measured was from about 1 to about 6 days. Where the external origination and/or destination temperatures were below the optimal internal temperature range for a particular product sought to be shipped such as below about 33° F. to about 46° F., gel packs having a higher temperature, e.g., about 59° F., were employed. Where the external origination and/or destination temperatures were above the optimal internal temperature range for a particular product sought to be shipped, such as above about 33° F. to about 46° F., such as for a refrigerated drug product, gel packs having a lower temperature, e.g., 5° F., were employed.

As one will appreciate, various insulation and temperature-maintaining materials can be used in accordance with the broad concept conveyed herein. For example, polyurethane foam can be used as the insulation, and a gel-forming polymer such as polyacrylate/polyalcohol copolymers can be used as the temperature-maintaining material. Various materials can be used for forming embodiments of containers in accordance with the invention and various sized containers may also be employed. However, standard cold shipping containers that are typically of a size that are used to deliver health care products, such as pharmaceutical products, are generally preferred. By way of example, the container may be a generally envelope-type enclosure, such as an Xpander Pak™. A large Xpander Pak™ is generally of a size of about 18 inches by 14 inches, and having a wall thickness of about 1⅜ inches. In an embodiment which employs an envelope-type enclosure, a cooling element, such as ice, is first placed into the envelope. A barrier element, such as a foam barrier, is then inserted into the envelope thereby creating two generally separate compartments, preferably mostly separate or fully separate compartments, one in which the cooling element is located, and the second being a space for an article to be placed. Generally, up to two products may be placed in an Xpander Pak that employs a liquid Gel Pak as the cooling element. Clearly, various other materials may be employed depending upon characteristics such as the intended operating temperature range, desired weight of the container, and stability/compatibility within the item(s) stored, among others. The selection of the particular materials is considered within the knowledge of one of skill in the art.

When the container is in the form of a cooler, it may be preferably a small cooler of size #1 which has dimensions of about 15 inches in length, by 11¼ inches in width, by 10¼ inches in height, with 2 inch thick walls. When the cooler is preferably a large cooler, such as a #7 N cooler, it will generally have the dimensions of 16¾ inches in length by 13¾ inches in width, by 11 inches in height, with 1½ inch thick walls. Thus, when the cooler is such as a foam cooler, at least one barrier or insulating element, such as a foam barrier or wall, may be inserted into the interior of a cooler to create at least two compartments within the cooler, one for receiving a cooling element, such as an ice pack, and the other for receiving at least one product.

Insulation that is incorporated into and/or forms the walls, top and/or bottom of a container may alternatively be formed, at least partially, of urethane and/or bio-based materials such as urethanes, e.g., soyoyl polyol, which are biodegradable. Thus, biodegradable containers that are suitable for one-time use may be employed. A biodegradable material, such as cardboard, could be used as an outer shell that protects the insulation. Insulating materials may also comprise bio-based polyurethanes. For instance, polyurethanes that comprise vegetable oil may be used. Bio-based insulating materials also can comprise starch, such as from potatoes, or can comprise other natural materials, such as limestone. Containers in accordance with the invention may include multiple material layers, and various materials and/or combinations of materials can be used to form each of the layers.

The material used to form the insulation of a container may also be used to form an outer shell of the container. In particular, various materials that form outer skins or hardened layers can be used. By way of example, ureas, e.g., urea polymers and/or copolymers, can be used to form insulated structures that incorporate hardened outer surfaces. Also, materials configured as foams can be used to form insulated structures with hardened outer surfaces. These hardened outer surfaces or skins typically form as the material contacts the form into which the material is placed.

As noted, various types of temperature-maintaining (cooling element) materials also can be used. By way of example, ice packs and Gel Packs (frozen and refrigerated) may be employed in any amount depending on the amount of ice or Gel contained in each pack. Typically, such ice and Gel Packs contain about 24 oz of ice or gel, respectively. When ice packs or Gel packs are employed, they will generally range in amounts of 1, 2, 3, 4, 5, 6, 7, 8, 9, or 10, packs. Frozen Gel Packs will typical have a temperature in a range of from about 5° F. to about 13° F., while refrigerated Gel packs will generally have a temperature in a range of from about 30° F. to about 46° F.

Alternative cooling elements may include, such as, acrylate-based superabsorbents. For instance, polacrylate/polyalcohol polymers and/or copolymers, such as AP85-38 manufactured by Emerging Technologies, Inc. of Greensboro, N.C., Norsocryl D-60, LiquiBlock, AT-03S, LiquiBlock 88, LiquiBlock 75, LiquiBlock 44-0C, among others can be used. In other embodiments, water and/or dry ice can be used in addition to, or in lieu of, other temperature-maintaining materials.

As described before, temperature-maintaining (cooling element) material can be incorporated into a container in various manners, such as by disposing the material between adjacent walls of the container and/or providing the temperature-maintaining materials in a package that can be placed within the interior of the container.

Thermally insulating materials that are useful according to this present invention include foams, such as polyurethanes, polystyrenes, or other foams as well porous insulation including fiberglass or porous silica.

Suitable desiccants include zeolites, barium oxide, activated alumina, silica gel, glycerine, magnesium perchlorate, calcium sulfate, calcium oxide, activated carbon, calcium chloride, alumina gel, calcium hydride, phosphoric anhydride, phosphoric acid, potassium hydroxide, sodium sulfate and bentonite clay.

Figure 6:
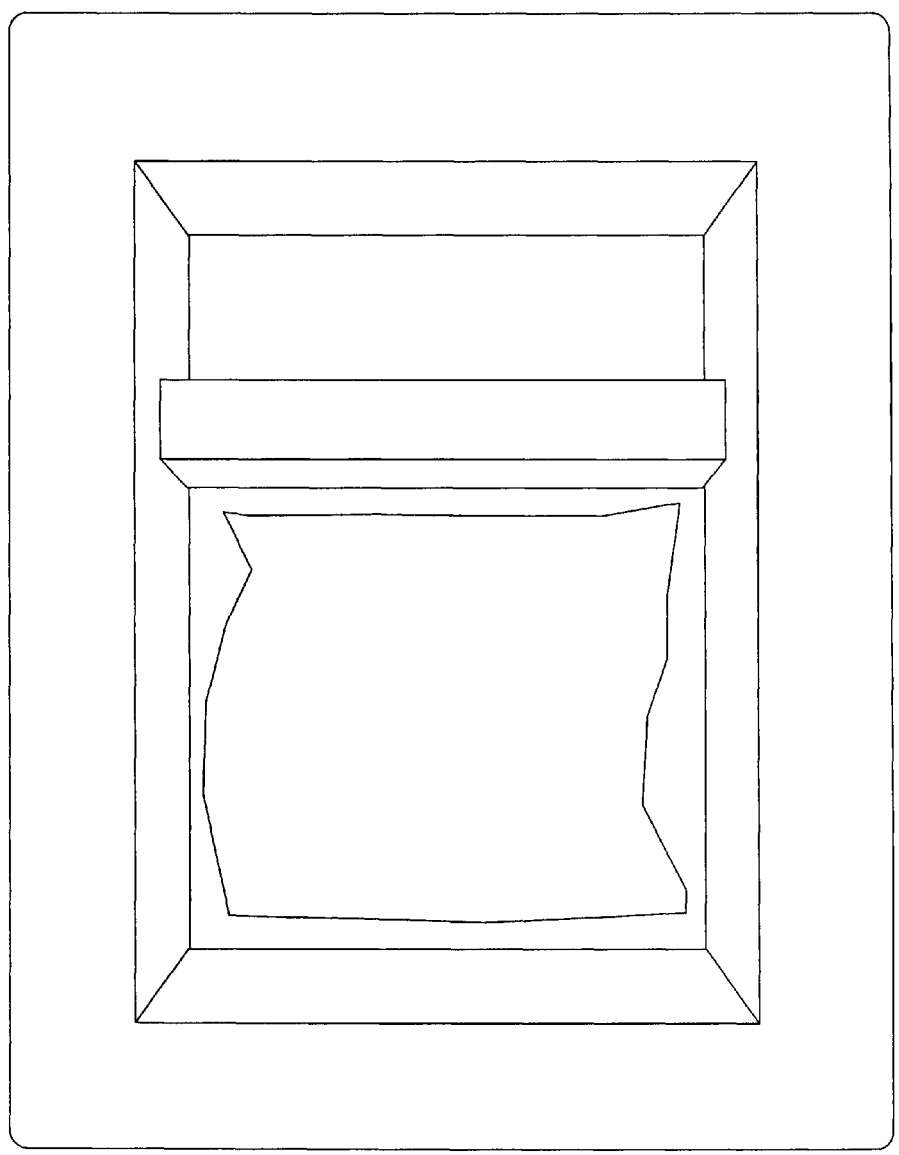
FIG. 6 is a top view illustration of a #1 cooler having a barrier wall, a product, and a cooling element, according to the invention.

As can be seen, FIGS. 1-4, show the general arrangements and the parameters for determining $a_1$ and $a_2$ according to the equation $(a_1)(k_1)(\Delta t_1)/th_1=(a_2)(k_2)(\Delta t_2)/(th_2)$ for an Xpander Pack, a #1 cooler, and a #7N cooler, respectively. FIGS. 5(a)-(g) show various packing arrangements that may be employed in accordance with the invention. As can be seen, a #1 cooler is packed with different amounts of cooling elements in different arrangements. The number and arrangement of cooling elements employed will depend on the type and amounts of products to be shipped, and the temperatures that the container is likely to be exposed to FIG. 6 illustrates an arrangement of a #1 cooler having a product to be shipped, a barrier wall positioned transversely and abutting two side walls, and several cooling elements, in accordance with determinations and arrangements achieved through the method of the invention.

Figure 7B:
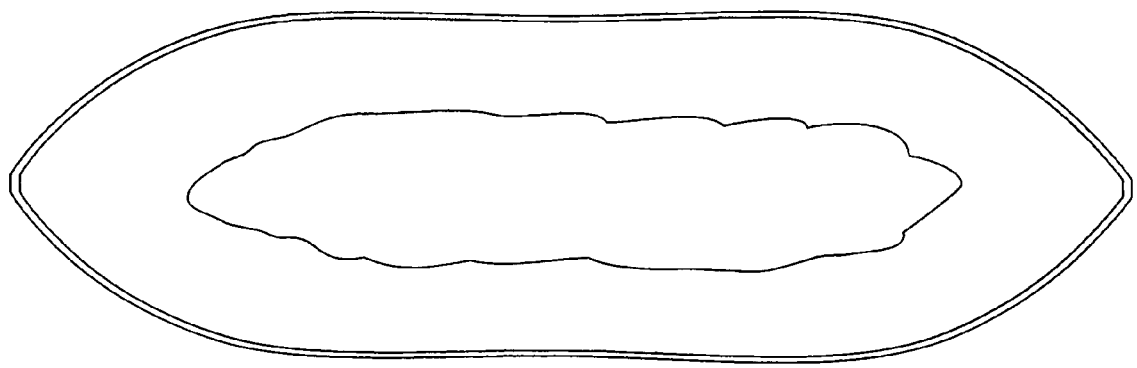
Figure 7C:
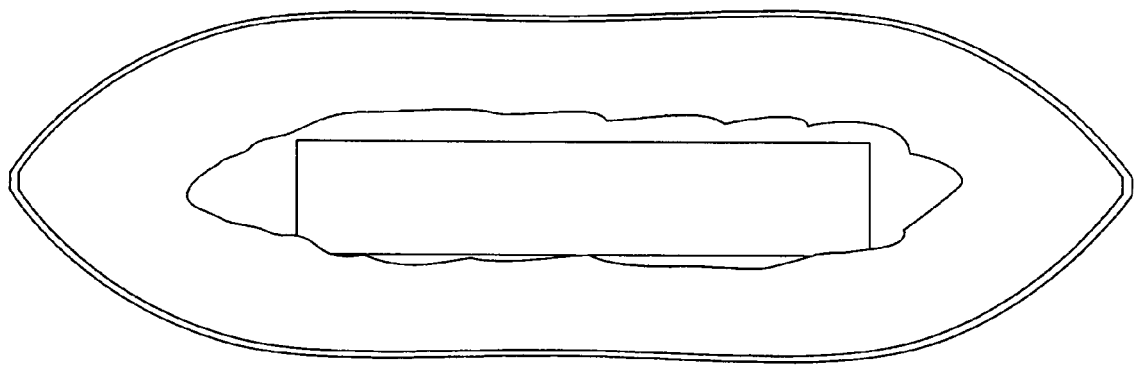

FIGS. 7(a)-(c) illustrate one embodiment of the preparation of an envelope-type container, known as an Xpander Pack, in accordance with the invention. As can be seen, in FIG. 7(a), the container is opened and a cooling element has been inserted into it. In FIG. 7(b), a barrier, made from a portion of another envelope, is inserted into the container to substantially seal off the cooling element from the product that will be inserted into the container. In FIG. 7(c), the product is finally inserted into the container.

FIG. 8 is a graph illustrating a container validation curve for a product requiring a temperature range of from about 33° F. to about 46° F. As can be seen, several #1 coolers and one Xpander Pack were packed with differing amounts of cooling elements, i.e., from 1-5 24 oz Gel Packs, having a starting temperature of 59° F. or 5° F. The number of days that each container was stored at a particular 10° F. temperature range, i.e., −15° F. to −5° F., −5° F. to 5° F., 5° F. to 15° F., 15° F. to 25° F., 25° F. to 35° F., 35° F. to 45° F., 45° F. to 55° F., 55° F. to 65° F., 65° F. to 75° F., 75° F. to 85° F., 85° F. to 95° F., 95° F. to 105° F., 105° F. to 115° F. and 115° F. to 125° F. was from 1-2 days. The internal temperatures of the containers were measured and found to be within the optimal temperature ranges.

FIG. 9 is a graph illustrating a freeze test using bottled water in a #1 cooler packed with 5 frozen gel packs having a temperature of about 5° F. As can be seen, while the exterior temperature remained at about 70° F., and 30° F. over about a 4 hour period.

FIG. 10 is a graph illustrating the relative temperature increases of combinations of cooling elements, i.e., from 1-10 24 oz Gel Packs, each having a starting temperature of 59° F., and over a period of 11 hours. As can be seen, the containers used included Xpander Packs, #1 coolers, and #7N coolers. The external temperature was constant and was that of normal plant facility temperature (e.g., about in a range of 63° F.-73° F. This illustrates the range of temperature that can be maintained generally by employing various amount of cooling elements having a starting temperature of about 59° F.

FIG. 11 is a graph illustrating a comparison of actual and projected empirical temperature ranges according to the invention. As can been seen, as Xpander Pack, a #1 cooler, and a #7N cooler were exposed to an external temperature that ranged between about 58° F. and 81° F. over a period of bout 3⅔ days. As also can be seen, the projected empirical results, calculated for each container and determined in accordance with the present invention match up well with the actual temperature range of between about 21° F. starting, and about 45° F. to about 72° F. after 3⅔ days.

The present application will be described in more detail with the aid of the examples which follow, which must be considered as illustrative and non-limiting.

EXAMPLES OF THE INVENTIONS

In general, a series of experiments were conducted to simulate and compare actual transport conditions to theoretical transport conditions for various embodiments according to the invention, and to determine the amount of cooling element that would be required to accompany a product in a package to achieve the desired product temperature range. Thus, in some experiments, to evaluate the benefits of the present invention, Xpander Packs and #1 and #7 N coolers were constructed as discussed above and were packed with ice packs on the cooling element side and a temperature probe sealed in a plastic bag on the product side in place of a product along with some paperwork. In addition, to simulate the stresses that a package generally encounters during transportation, the test packages were then placed outside in the heat for a period of time, and then were moved inside of a car to be subjected to the heat that occurs inside of a car for another period of time.

Experiments that were carried out with #1 and #7 N coolers employed bubble wrap to fill any empty space in the coolers and maintain the position of the foam barrier element. Tests using multiple coolers were usually run concurrently and an external temperature probe was taped to the exterior surface of the cooler. The packages were placed outside, usually out of direct sunlight, and at the end of the day the packages were transferred into an automobile. The software program discussed above was employed to determine the amount of ice and hence ice packs, that were needed to be inserted into the container, and the thickness of the foam wall to be employed in each package was determined from the following examples.

Example 1

Three 24 oz ice packs, as determined by the software program employed, were placed into a standard Xpander Pak and a foam barrier, made from another Xpander Pak, was placed adjacent the ice packs. A temperature probe was placed in the Xpander Pak on the product side in place of a product and the package was sealed. An external temperature probe was employed to measure the temperatures at which the package was exposed. The package was exposed to temperatures that ranged from a high of 91.8° F. to a low of 70.8° F. for a period of about 15 hours and 18 minutes. A separate #1 cooler was similarly constructed with a foam barrier, made from an Xpander Pak, placed adjacent three 24 oz ice packs, as determined by the software program employed, which were placed into the cooler. The cooler was then exposed to the same temperature conditions for a period of about 15 hours and 13 minutes.

Example 2

To determine whether the particular packaging method would cause the product side of the package to become too cold, such as might be encountered on cooler days of transport, three 24 oz ice packs, as determined by the software program employed, were placed into a standard Xpander Pak and a foam barrier, made from another Xpander Pak, was placed adjacent the ice packs. A temperature probe was placed in the Xpander Pak on the product side in place of a product and the package was sealed. An external temperature probe was employed to measure the temperatures at which the package was exposed. The package was exposed to temperatures that ranged from a high of 76.8° F. to a low of 71.8° F. for a period of about 88 hours and 33 minutes. A separate #1 cooler was similarly set up, except that the barrier wall was made from the wall of another #1 cooler (about 1.25 inches thick), and exposed to the same temperatures for a period of about 88 hours and 40 minutes. In a separate #7 cooler, five 24 oz ice packs were employed, as determined by the software program, and the barrier wall was made from the wall of another #1 cooler. The cooler was otherwise was similarly set up and exposed to the same temperatures for a period of about 88 hours and 39 minutes. The barrier wall was determined to be too thick from the experiment with the #7N cooler, so the wall was adjusted accordingly to make the cooling element compartment smaller.

Example 3

A #1 cooler was packed with three 24 oz ice packs as determined by the software program employed. Initially, the insulating barrier was placed at a position two inches away from the medication end of the cooler based upon the size of the product to be placed into the package. However, the barrier was thereafter adjusted to a position exactly where the cooling element ended. Based on the adjusted surface area of the medication compartment, the program predicted that the barrier element's thickness should be reduced from about 1.25 inches to about 0.75 inches. In another test procedure, only the area of the cooling element compartment area was employed in the program. The program still reported that three 24 oz packs of ice should be employed. The package was then exposed to temperatures that ranged from a high of 117.9° F. to a low of 73.8° F. for a period of about 26 hours and 37 minutes While various embodiments have been shown and described, it should be understood that a number of changes and modifications are possible therein. Accordingly it is to be understood that there is no intention to limit the inventions to the precise constructions and methods, disclosed herein, and the right is reserved to all changes and modifications coming within the scope, literally or equivalently, of the invention as defined in the appended claims.

What is claimed is:

1. A method comprising:
   identifying, on a processor, an acceptable temperature range of a temperature sensitive health care product, the acceptable temperature range being based on a temperature range at which the temperature sensitive product maintains freshness and efficacy;
   identifying, on the processor, a forecasted temperature associated with a product origin location of the temperature sensitive health care product;
   identifying, on the processor, a forecasted temperature associated with a product destination location of the temperature sensitive health care product;
   identifying, on the processor, an anticipated transit duration of the temperature sensitive health care product; and
   determining, on the processor, a quantity of temperature control elements having a starting temperature to include in a shipping container to maintain the acceptable temperature range of the temperature sensitive health care product within the shipping container based on the forecasted temperature associated with the product origin location, the forecasted temperature associated with the product destination location, the anticipated transit duration, and a barrier element located within the shipping container, the barrier element separately maintaining the quantity of temperature control elements and the temperature sensitive health care product in the shipping container.

2. The method of claim 1, wherein the quantity of temperature control elements includes a gel pack having the starting temperature in the range of about 59° F. to about 5° F.

3. The method of claim 1, wherein a determination of the quantity of temperature control elements to include in the shipping container is not based on designation or selection of a shipping route taken between the product origin location and the product destination location.

4. The method of claim 1, further comprising:
   recording shipment of the temperature sensitive health care product in the shipping container, the shipping container including the quantity of temperature control elements.

5. The method of claim 4, further comprising:
   receiving a shipment request,
   wherein a determination of the quantity of temperature control elements is in response to receipt of the shipment request.

6. The method of claim 1, wherein identifying the forecasted temperature associated with the product origin location comprises:
   transmitting a weather forecast request including a shipment start date and the product origin location; and
   receiving the forecasted temperature associated with the product origin location in response to transmission of the weather forecast request.

7. The method of claim 1, wherein the temperature range is from about 59° F. to about 86° F.

8. The method of claim 1, wherein the quantity of temperature control elements includes a heating element.

9. The method of claim 1, wherein the barrier element separately maintains the quantity of temperature control elements and the temperature sensitive health care product in fully separate compartments of the shipping container.

10. The method of claim 1, wherein the barrier element separately maintains the quantity of temperature control elements and the temperature sensitive health care product in mostly separate compartments of the shipping container, the mostly separate compartments not being full separate compartments.

11. The method of claim 1, wherein the barrier element is a foam barrier.

12. The method of claim 1, wherein determination of the quantity of temperature control elements to include in the shipping container is not based on a route taken between the product origin location and the product destination location.

13. The method of claim 1, wherein the route is an actual route.

14. The method of claim 1, wherein the route is a predetermined route.

15. The method of claim 1, further comprising;
   transmitting notification of shipment of the temperature sensitive health care product in the shipping container, the shipping container including the temperature control elements.

16. The method of claim 1, wherein the temperature range is from about 36° F. to about 46° F.

17. The method of claim 1, wherein the quantity of temperature control elements includes a cooling element.

18. The method of claim 1, wherein during a shipping process of the temperature sensitive health care product within the shipping container, acquired heat is transferred from the temperature sensitive health care product through the barrier element to at least one temperature control element, the at least one temperature element including at least one of the quantity of temperature control elements.

19. The method of claim 18, wherein the transfer of the acquired external environment heat from the temperature sensitive health care product to the at least one temperature control element occurs at a controlled rate through the barrier element.

20. The method of claim 18, wherein the heat includes external environment heat.

21. The method of claim 1, wherein during a shipping process of the temperature sensitive health care product within the shipping container, acquired heat is transferred to the temperature sensitive health care product through the barrier element from at least one temperature control element, the at least one temperature element including at least one of the quantity of temperature control elements.

22. The method of claim 1, wherein the shipping container includes a shipping envelope.

23. The method of claim 1, wherein the shipping container includes a cooler.

24. A non-transitory machine-readable medium comprising instructions, which, when executed by one or more processors, cause the one or more processors to perform the following operations:

identify an acceptable temperature range of a temperature sensitive health care product, the acceptable temperature range being based on a temperature range at which the temperature sensitive product maintains freshness and efficacy;

identify a forecasted temperature associated with a product origin location of the temperature sensitive health care product;

identify a forecasted temperature associated with a product destination location of the temperature sensitive health care product;

identify an anticipated transit duration of the temperature sensitive health care product; and determine a quantity of temperature control elements having a starting temperature to include in a shipping container to maintain the acceptable temperature range of the temperature sensitive health care product within the shipping container based on the forecasted temperature associated with the product origin location, the forecasted temperature associated with the product destination location, the anticipated transit duration, and a barrier element located within the shipping container, the barrier element separately maintaining the quantity of temperature control elements and the temperature sensitive health care product in the shipping container.

* * * * *